(12) United States Patent
O'Brien

(10) Patent No.: US 8,684,945 B2
(45) Date of Patent: Apr. 1, 2014

(54) DIGITAL TUNING FORK FOR SENSATION TESTING DEVICE

(76) Inventor: Todd O'Brien, Orono, ME (US)

( * ) Notice: Subject to any disclaimer, the term of this patent is extended or adjusted under 35 U.S.C. 154(b) by 390 days.

(21) Appl. No.: 13/207,922

(22) Filed: Aug. 11, 2011

(65) Prior Publication Data

US 2012/0046580 A1     Feb. 23, 2012

Related U.S. Application Data

(60) Provisional application No. 61/375,527, filed on Aug. 20, 2010.

(51) Int. Cl.
*A61B 5/00*     (2006.01)

(52) U.S. Cl.
USPC .......................................................... 600/552

(58) Field of Classification Search
CPC ....... A61B 5/0051; A61B 5/16; A61B 5/4827
USPC .......................................................... 600/552
See application file for complete search history.

(56) References Cited

U.S. PATENT DOCUMENTS

| | | | | |
|---|---|---|---|---|
| 5,002,065 A | * | 3/1991 | LaCourse et al. | 600/552 |
| 2011/0112431 A1 | * | 5/2011 | Golosarsky et al. | 600/552 |

* cited by examiner

*Primary Examiner* — Max Hindenburg
*Assistant Examiner* — Jonathan M Foreman
(74) *Attorney, Agent, or Firm* — Anthony D. Pellegrini

(57) ABSTRACT

An improved digital tuning fork device for administering a vibratory sensation test to a human subject comprising an integrated vibratory mechanism and timer, with the vibratory mechanism generating vibrations having a known frequency and amplitude, with the amplitude of the vibrations degrading over time to replicate in a controlled manner the natural degradation of vibrations generated by a mechanical tuning fork, and a method of use thereof.

20 Claims, 2 Drawing Sheets

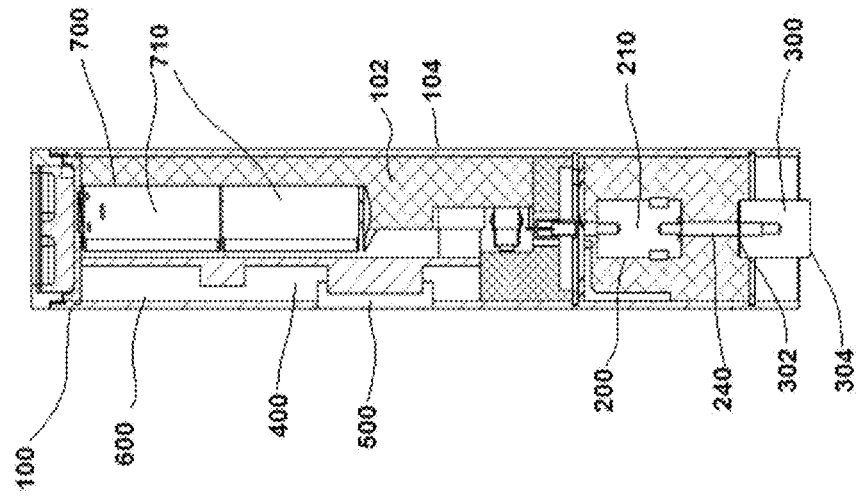
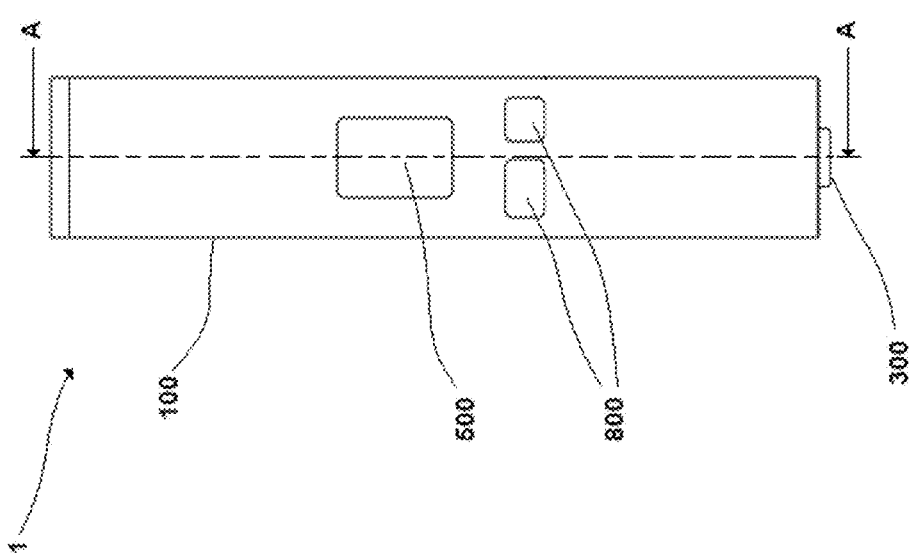

DIGITAL TUNING FORK FOR SENSATION TESTING DEVICE

CROSS REFERENCE TO RELATED APPLICATION

This application claims priority to a provisional application, U.S. Ser. No. 61/375,527, filed Aug. 20, 2010, entitled Digital Tuning Fork for Sensation Testing Device, by O'Brien, Todd, which is hereby incorporated by reference.

BACKGROUND OF THE INVENTION

1. Technical Field

The present invention relates generally to medical diagnostic devices and more specifically it relates to a device for testing sensation by means of placing a vibratory apparatus against a human body part.

2. Description of Prior Art

The present invention discloses a vibratory device to be placed onto a human body part, such that the perception (or lack of perception) of the vibrations by the human subject indicates a degree of sensitivity to touch in that body part. Such testing is useful in diagnosing peripheral neuropathy in the extremities, such as the feet. Peripheral neuropathy (i.e., damage to nerves of the peripheral nervous system) is a common cause of foot ulcers in diabetics, resulting in the loss of protective sensation. A frequent consequence of diabetic foot ulcers is lower extremity amputation. It is well established that diabetic foot ulcers precede amputation in most instances. The Center for Disease Control and Prevention recently estimated the prevalence of diabetes in the United States at 8% of the population. The World Health Organization forecasts that the worldwide prevalence of diabetes will double by the year 2030. In light of these staggering numbers and their attendant human and financial costs, a concerted effort is under way to treat diabetes and prevent its subsequent complications.

Simple screening tests for diabetic peripheral neuropathy have been performed for decades to assess sensation in the feet of diabetic patients. The goal of these tests is to appropriately identify those patients with a loss of protective sensation. Once the diagnosis is made, preventative interventions such as palliative podiatric care, specialized shoe wear, and surgery can be initiated. These interventions can prevent diabetic foot ulcers which lead to subsequent infections, hospitalizations and amputations.

The two most common screening tools are the Semmes-Weinstein 10 gram nylon monofilament and the 128 Hertz tuning fork. The nylon monofilament is designed to buckle when 10 grams of force is applied to the skin. The test is performed on various anatomic locations on the bottom of the patient's foot. If the patient is unable to perceive the monofilament at any location, they are deemed to have a loss of protective sensation putting them at risk for foot ulcers. Although the use of this test is widespread, its accuracy and validity have been called into question. It has long been known that nylon monofilaments undergo fatigue with use, rendering them unable to consistently apply 10 grams of pressure. Another complicating factor is the frequent presence of calluses on the bottom of a patient's feet which falsely can mimic neuropathy when only slight pressures are applied.

The 128 Hz tuning fork is an alternative to the nylon monofilament test. It has also been used for decades to assess diabetic peripheral neuropathy and is generally known to be more sensitive than other screening methods. The test is conducted by striking a tuning fork on a solid object and then touching the base of the tuning fork to a bony prominence on the patient's foot. The patient will then perceive (or not) a vibration which gradually subsides over time. The patient tells the clinician when they are no longer able to perceive the vibrations. If the clinician can still feel the vibrations after the patient cannot, then the patient is deemed to have diminished vibratory sensation. Research has shown that patients who are able to feel the tuning fork vibrations for four seconds or less have severe diabetic peripheral neuropathy and are at risk for foot ulceration. Because the vibrations from the tuning fork will propagate through tough or callused skin, use of this test avoids the significant disadvantage of the monofilament test. A tuning fork will also not degrade as will a nylon monofilament, so it can be used over and over without need for replacement.

Despite the better accuracy of the tuning fork test, the use of traditional tuning forks involves an unacceptable degree of subjectivity. Specifically, the force of the initial strike of the tuning fork against the solid object will vary from clinician to clinician and even from one administration of the test to another by the same clinician. The pressure of the end of the tuning fork against the body part may also vary. Either or both of these factors can impact the strength of the initial vibration and thus the time of subsidence of the vibration (whereby a stronger initial vibration will be felt for a longer period of time than a weaker initial vibration). Finally, the exact time of sensation is difficult to precisely determine, either because a simple wall clock is used or another person is required to operate a stop watch.

One device used in an attempt to remove subjectivity from the tuning fork test is known as a biothesiometer. A biothesiometer is a sophisticated vibration testing device involving a contact component, a meter, and an external power supply. It electronically controls a vibration, having means for adjusting the amplitude to determine a sensory threshold. The user either sets a predetermined amplitude and determines whether the patient perceives sensation, or sets the device to either a low amplitude or a high amplitude and then either increases or decreases the amplitude, as appropriate, until the patient first perceives the sensation or stops perceiving the sensation. While the use of a biothesiometer is considered the gold standard in vibration testing, because of its expense and complexity it is little used in most medical offices.

It is therefore shown that there is a need for an improved device for administering a vibratory sensation test having the advantages of the traditional tuning fork test while minimizing the subjectivity inherent in traditional tuning fork tests.

It is therefore an object of the present invention to provide an improved device for administering a vibratory sensation test to a portion of the human body.

Another object of the present invention is to provide an improved device that provides the advantages of a traditional tuning fork test.

Another object of the present invention is to provide an improved device that provides a uniform initial vibration each time it is utilized.

Another object of the present invention is to provide an improved device that provides a uniform degradation of vibration over time each time it is utilized.

Another object of the present invention is to provide an improved device that is integrated with a timer.

Another object of the present invention is to provide an improved device that provides quantifiable, objective information to the clinician.

Another object of the present invention is to provide an improved device that is easy to use.

Another object of the present invention is to provide an improved device that is easy and inexpensive to manufacture.

Other objects and advantages of the present invention will become obvious to the reader and it is intended that these objects and advantages are within the scope of the present invention. To the accomplishment of the above and related objects, this invention may be embodied in the form illustrated in the accompanying drawing. Attention being called to the fact, however, that the drawing is illustrative only, and that changes may be made in the specific construction illustrated and described within the scope of this disclosure.

BRIEF SUMMARY OF THE INVENTION

The present invention comprises a housing in which is contained an electronic vibratory mechanism, a timer, a power supply, and a controller. The controller controls the activation, operation, and deactivation of the vibratory mechanism and the timer. Integrated with the housing and partially extending therefrom is an elongate contact member. The contact member is suitably adapted to transmit vibrations generated by the vibratory mechanism along its length to its terminal external end, which may be placed against a human body part. In one embodiment, the internal end of the contact member may also be adapted to engage with the controller. In such an embodiment the contact member is disposed in an extended orientation by a spring mechanism; when so oriented, the contact member is maximally extended from the housing and disengaged from the controller, and the vibratory mechanism and the timer are in an inactive state. When the contact member is pressed against the body part it is moved against the bias of the spring mechanism and into the housing until it engages with the controller, causing the initiation of the operation of the vibratory mechanism and the timer. When the contact member is removed from the body part it is biased by the spring mechanism to its extended orientation and the operation of the vibratory mechanism and the timer is terminated. The timer may be reset by the controller for the next application of the test. In other embodiments the user signals the controller to activate and deactivate the vibratory mechanism and timer by the use of user control buttons. One button, for example, may be used to start and stop the vibratory mechanism and timer, and another button may be used to reset the timer. Yet another button may be used as a master power switch. Other user input configurations are also contemplated. Integrated with the housing may be a mechanism for facilitating holding the device in a human hand.

During use, the device will be placed against the patient's body and then will begin its vibrating and timing functions. The vibration will continue with a predetermined degradation of amplitude (i.e., strength of vibrations), providing ever diminishing vibratory sensations. When the patient can no longer feel the vibrations he or she so indicates and the device is removed from the patient's body and the vibrations and timer stop. The clinician can then read the time on the integrated timer display. The time is then compared against a database of known normal and abnormal timed vibration tests used to provide clinical guidelines. A cut off value in seconds may be established enabling clinicians to more accurately assess those at risk for foot ulcers.

There has been outlined, rather broadly, some of the features of the invention in order that the detailed description thereof may be better understood, and in order that the present contribution to the art may be better appreciated. There are additional features of the invention that will be described hereinafter.

In this respect, before explaining at least one embodiment of the invention in detail, it is to be understood that the invention is not limited in its application to the details of the construction or to the arrangements of the components set forth in the following description or drawing. The invention is capable of other embodiments and of being practiced and carried out in various ways. Also, it is to be understood that the phraseology and terminology employed herein are for the purpose of the description and should not be regarded as limiting.

Various other objects, features and attendant advantages of the present invention will become fully appreciated as the same becomes better understood when considered in conjunction with the accompanying drawings.

BRIEF DESCRIPTION OF THE DRAWING

FIG. 2A depicts a plan side view of the present invention.
FIG. 2B depicts a plan side cut-away view of the present invention along the line A-A as shown in FIG. 2A.

DETAILED DESCRIPTION OF THE INVENTION

Figure 1:
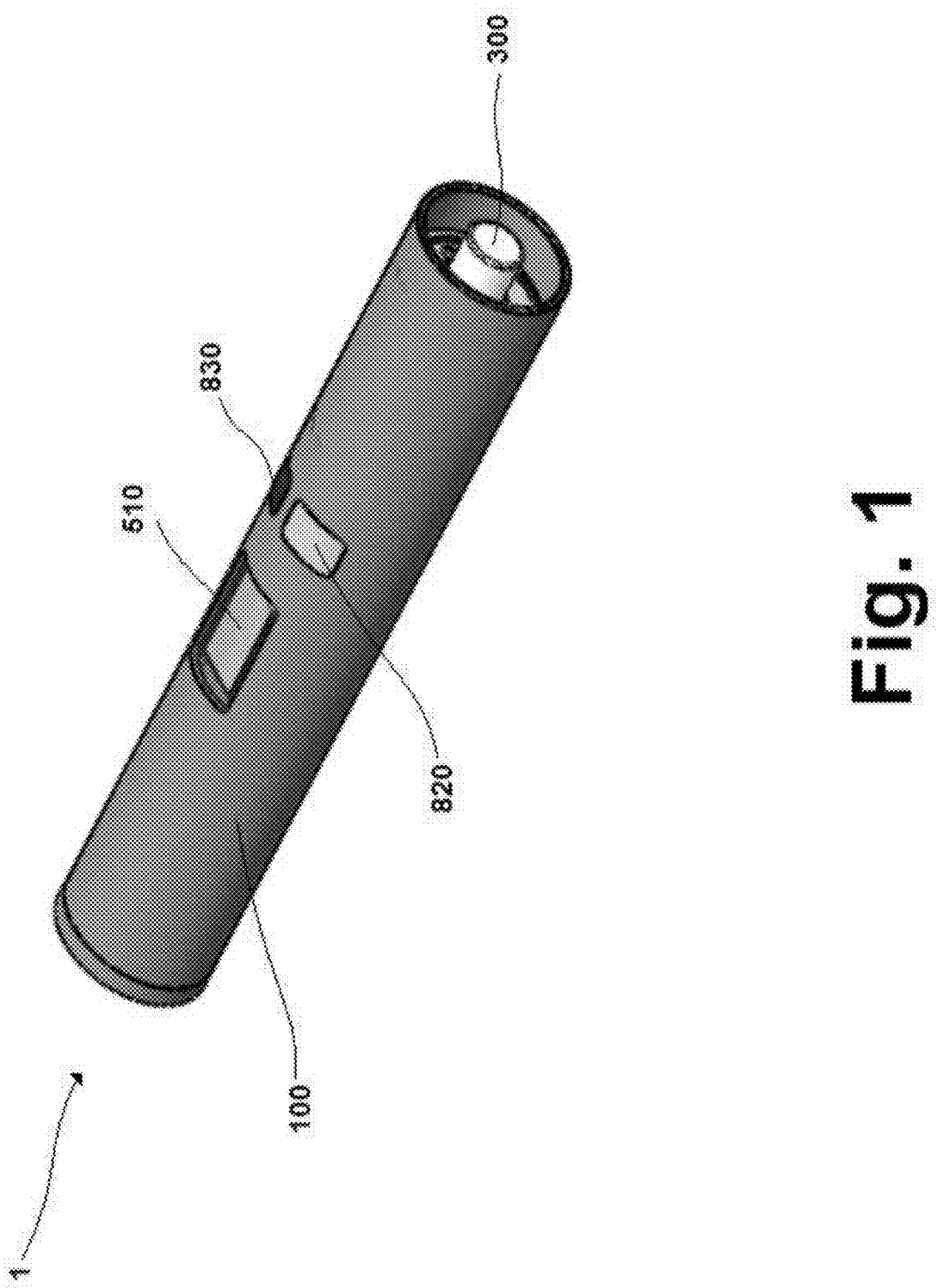
FIG. 1 depicts a perspective view of the present invention.

The housing 100 of the present invention 1 is small enough to be easily held by a human hand. It is substantially hollow, having an interior 102 and an exterior 104. The housing 100 may be constructed of any substantially rigid, durable material, such as plastic, metal, composites, or the like. It may have any suitable shape, such as substantially cubic, spherical, cylindrical, or it may be of an irregular shape. The housing 100 must have a means of communication between its exterior 104 and interior 102. In one embodiment the communications means is one or more apertures. In another embodiment the means may be an electronic circuit. The housing 100 should also have a means of accessing its interior 102, for ease of assembly and for maintenance purposes, such as changing a battery 710. This means may be a removable panel, or the housing 100 itself may separate into components which may then be reattached to each other, by tabs or threads or other means known in the art. Integrated with the housing 100 may be a handle or other device for facilitating holding the device 1 by a human hand. In one embodiment the housing 100 has an integrated ring which can be placed over a human finger. When so placed, the housing 100 depends from the finger and is proximate to the palm of the hand, whereby the fingers of the hand may grasp the housing 100.

The electronic vibratory mechanism 200 is contained within the interior 102 of the housing 100 and is suitably adapted to vibrate at a known frequency. In the preferred embodiment the frequency is 128 Hz, though other frequencies are also contemplated. The initial amplitude (e.g., strength) of the vibration is predetermined, with the amplitude of the vibrations decreasing in a known manner over a period of time. The degradation of the vibrations may be designed to replicate the natural degradation of vibrations of a mechanical tuning fork, though different degradation patterns may be used, as desired. The vibratory mechanism 200 is suitably adapted to being activated and deactivated by the controller 600, and is powered by the power supply 700.

The vibratory mechanism 200 is preferably an electric motor. In the preferred embodiment the vibratory mechanism 200 comprises a combination electric linear motor coil and magnet 210. Other devices may be used to generate vibrations, including audio speakers, piezo-electric speakers, piezo-electric linear bending actuators, piezo-electric mass excitation devices (as is used in ultrasonic welding devices), rotary electric motors driving weights, linkages (such as a Stephenson's linkage), magnetic thrust devices (such as the electromagnet used in biothesiometers), and other devices.

In the preferred embodiment the vibratory mechanism 200 is coupled to the contact member 300 by a vibratory transfer means. The vibratory transfer means should be a low lash motion transfer mechanism with sufficient travel and robustness to provide high axial stiffness while remaining compliant along the motion axis.

The controller 600 is contained within the interior 102 of the housing 100 and is suitably adapted to receive input from the exterior 104 of the housing 100 in order to control the activation, operation, and deactivation of the vibratory mechanism 200 and the timer 400. The controller 600 may be an integrated component of the vibratory mechanism 200, or it may be a separate component in communication with the vibratory mechanism 200, such as a printed circuit board, or even just a mechanical switch. The controller 600 ensures that the vibrations created by the vibratory mechanism 200 are generated at the correct frequency and originate at a defined amplitude, which then decreases in a known manner. It also ensures that the timer 400 is simultaneously activated with the activation of the vibratory mechanism 200 and simultaneously deactivated with the deactivation of the vibratory mechanism 200. Other extended features may also be controlled by the controller 600. For example, the controller 600 may be used to dynamically set the frequency of the vibrations to be generated by the vibratory mechanism 200, dynamically change the initial amplitude of the vibrations, or to change the manner in which the amplitude of the vibrations generated by the vibratory mechanism 200 decrease over time.

The contact member 300 provides an interface between the vibratory mechanism 200 and the patient. The contact member 300 is substantially rigid and elongate, having an internal end 302 located within the interior 102 of the housing 100 and an external end 304 located exterior of the housing 100. In the preferred embodiment the contact member 300 is substantially cylindrical. Vibrations generated by the vibratory mechanism 200 are transmitted to the patient through the contact member 300 from its internal end 302 along its length to its external end 304.

In one embodiment the contact member 300 is suitably adapted to engage with the controller 600. In this embodiment the contact member 300 is movable relative to the housing 100 and may move partially in and out of the housing 100. The contact member 300 may be disposed in an extended orientation (meaning relatively more of the contact member 300 is located exterior of the housing 100) by a spring mechanism. A force applied to the external end 304 of the contact member 300 will bias the contact member 300 against the spring mechanism, moving relatively more of the contact member 300 into the interior 102 of the housing 100. Removing the force allows the spring mechanism to bias the contact member 300 to its extended orientation. The spring mechanism may be a coil spring, a hinge spring, compressible foam, or any other mechanism known in the art having the ability to bias the contact member 300 to its extended orientation. In this embodiment the internal end 302 of the contact member 300 is disengaged from the controller 600 when the contact member 300 is in its extended orientation. When the contact member 300 is so oriented, the controller 600 is not activated and the vibratory mechanism 200 and the timer 400 are in an inactive state. When the contact member 300 is moved into the housing 100 by an application of force to its external end 304, the internal end 302 of the contact member 300 engages the controller 600 causing the controller 600 to activate the vibratory mechanism 200 and the timer 400. The vibrations generated by the vibratory mechanism 200 are transmitted along the contact member 300 to the patient's body part. When the contact member 300 is moved back to its extended orientation it disengages from the controller 600 causing the operation of the vibratory mechanism 200 and the timer 400 to be terminated.

In an alternative embodiment of the invention, the contact member 300 is a touch sensitive plate in electronic contact with the controller 600 and in physical contact with the vibratory mechanism 200. When the contact member 300 is touched against the patient's body part an electronic signal is sent to the controller 600 which activates the vibratory mechanism 200 and timer 400. The vibratory mechanism 200 then transmits vibrations through the contact member 300 to the patient's body part. When contact between the patient and the contact member 300 ceases, the controller 600 deactivates the vibratory mechanism 200 and stops the timer 400.

In yet another alternative embodiment of the invention, the device 1 uses one or more user input controls 800 to control operation of the vibratory mechanism 200 and the timer 400. The user input controls 800 are in connection with the controller 600 and are suitably adapted to allow a user to signal when the power supply 700 is to be activated and deactivated, when the vibratory mechanism 200 is to be activated and deactivated, when the timer 400 is to be activated and deactivated, and when the display means 500 is to be reset. In this embodiment the user input controls 800 may be a series of push buttons. Other controls may also be used, such as touch sensitive buttons, sliders, knobs, dials, and the like, or any combination thereof. One example employs a power button adapted to activate and deactivate the main power supply 700, an enable button 820 adapted to activate the timer 400 and simultaneously activate the vibratory mechanism 200 when pressed and to deactivate the timer 400 and simultaneously deactivate the vibratory mechanism 200 when released, and a reset button 830 adapted to reset the timer display 500. Other user control inputs may also be used for extended functionality of the device 1. For example, a frequency selection button might be used to allow a user to change the frequency of the vibrations generated by the vibratory mechanism 200, an amplitude selection button might be used to allow a user to change the beginning amplitude of the vibrations generated by the vibratory mechanism 200, or a degradation selection button might be used to allow a user to change the manner in which the amplitude of the vibrations generated by the vibratory mechanism 200 decrease over time. Each of these buttons may be step functions, whereby each press changes the function to the next predetermined setting. Alternatively, these functions may be embodied in knobs or dials or sliders which permit a continuum of selection possibilities.

The timer 400 is contained within the interior 102 of the housing 100 and is suitably adapted to record the relative passage of time beginning from zero. The units of time recorded by the timer 400 should be sufficiently small in order to provide accurate differentiation between tests. In one embodiment the units of time may be tenths of seconds. In another embodiment the units of time are hundredths of seconds. The timer 400 must have a visible display 500 to show the units of time being counted as well as the final amount of time at the completion of the test. The timer display 500 may use any practical component known in the art, such as an LED ("light emitting diode") 510 or an LCD ("liquid crystal display"). The display 500 should be visible from the exterior 104 of the housing 100. This may be accomplished by the housing 100 being transparent, or having a transparent portion over the display 500, or having an opening over the display 500. In the preferred embodiment the timer display 500 is placed within an opening in the exterior 104 of the housing 100. The final time reading at the completion of a test may remain visible for a predetermined amount of time and then automatically reset to zero (or go blank), or it may require a manual reset. When a manual reset is required the timer 400 may be reset by an independent control, such as a reset button 830. In one embodiment the timer 400 is reset upon reactivation of the timer 400. The timer 400 is adapted to being started and stopped by the controller 600, and is powered by the power supply 700. In an alternative embodiment the timer 400 has its own power supply 700 independent from the vibratory mechanism 200.

The power supply 700 is contained within the interior 102 of the housing 100 and is suitably adapted to provide power to the vibratory mechanism 200 and to the timer 400. The preferred power supply 700 is a replaceable battery 710, though a rechargeable battery or other suitable power supply 700 may be used. Multiple batteries 710 may also be used. Alternatively, the power supply 700 may be a combination of a power cord that connects the device 1 to an electrical outlet and a transformer used to step down the voltage supplied by the electrical outlet. The power supply 700 may be comprised of multiple sub-power supplies. In one embodiment a first power supply provides power to the vibratory mechanism 200 while a second power supply provides power to the timer 400.

A method of use for the present invention is also disclosed herein, comprising the following steps:

Step A. Obtain an improved digital tuning fork device 1 of the present invention;

Step B. uncover a portion of a patient's body so that the outer skin is revealed;

Step C. take the device 1 in hand;

Step D. place the device 1 against the uncovered portion of the patient's body;

Step E. activate the vibratory mechanism 200 and timer 400;

Step F. wait for the patient to indicate a lack of perception of sensation from the vibrations;

Step G. deactivate the vibratory mechanism 200 and stop the timer 400;

Step H. remove the device 1 from contact with the patient's body part;

Step I. note the time displayed on the timer display 500; and

Step J. compare the time displayed on the timer display 500 against known values.

In the preferred embodiment step B is performed in any order relative to steps A and C; step A must be performed before step C; steps A through C must be performed before step D; steps D and E may be performed in any order relative to each other; steps D and E must be performed before step F; steps G and H may be performed in any order relative to each other; step F must be performed before steps G and H; steps I and J must be performed after step G; and step J must be performed after step I. In alternative embodiments step B may be eliminated and step D may involve placing the device 1 against a covered body part; step C may include placing the optional finger ring over a finger of the hand; step F may be accomplished by a verbal indication, a hand signal, eye blinks, or other means agreed upon between the clinician and the patient; step J may be accomplished by looking up values in a text book, log book, treatise, computerized database, or the like; and an optional Step K may be added following Step J, by which a diagnosis is made. In an embodiment of the device 1 in which movement of the contact member 300 signals the controller 600, steps D and E are combined wherein the placing of the device 1 against the uncovered portion of the patient's body causes activation of the vibratory mechanism 200 and timer 500; similarly, steps G and H are combined wherein the removal of the device 1 from contact with the patient's body part causes deactivation of the vibratory mechanism 200 and timer 500. In an embodiment of the device 1 in which user input controls 800 are present, steps E and G are accomplished by use of the user input controls 800.

What has been described and illustrated herein is a preferred embodiment of the invention along with some it its variations. The terms, descriptions and figures used herein are set forth by way of illustration only and are not meant as limitations. Those skilled in the art will recognize that many variations are possible within the spirit and scope of the invention in which all terms are meant in their broadest, reasonable sense unless otherwise indicated. Any headings utilized within the description are for convenience only and have no legal or limiting effect. Other embodiments not specifically set forth herein are also within the scope of the following claims.

I claim:

1. A digital tuning fork device for administering a vibratory sensation test to a human subject, comprising a housing,
    said housing being substantially hollow, having an interior and an exterior, constructed of a substantially rigid, durable material, and having a shape suitable for being grasped by a human hand;

a vibratory mechanism,
    said vibratory mechanism being contained within the interior of the housing, said vibratory mechanism being electronically powered and suitably adapted to create variable amplitude vibrations at a constant frequency, and further suitably adapted to provide vibrations with amplitudes which decrease in a defined manner over a period of time;

a contact member,
    said contact member being substantially elongate and rigid and having an internal end located within the interior of the housing and an external end located exterior of the housing, said internal end suitably adapted to receive vibrations created by the vibratory mechanism and said external end suitably adapted to transmit vibrations to the human subject;

a timer,
    said timer being contained within the interior of the housing, said timer being suitably adapted to record the relative passage of time in known units beginning when activated and terminating when deactivated, said timer having a display means for displaying the units of time during activation and the final unit achieved upon deactivation, said display means being capable of being perceived from the exterior of the housing;

a controller,
    said controller being contained within the interior of the housing and being suitably adapted to receive input from the exterior of the housing, said controller being suitably adapted to activating and deactivating the vibratory mechanism, activating and deactivating the timer, and resetting the timer; and a power supply,
    said power supply being contained within the interior of the housing and being suitably adapted to provide power to the vibratory mechanism and to the timer;

wherein the contact member is movable in relation to the housing, said contact member having a spring to bias the external end of the contact member away from the housing, said contact member being in connection with controller, with movement of the contact member relative to the housing suitably adapted to signal the controller,
such that when the contact member is pressed against a surface the external end of the contact member moves toward the housing causing the contact member to signal the controller to reset the display means, to activate the vibratory mechanism, and to activate timer, and
when the contact member is removed from a surface the biasing spring moves the external end of the contact member away from housing causing the contact member to signal the controller to deactivate the vibratory mechanism and to deactivate timer.

2. The device of claim 1 wherein the vibratory mechanism comprises an electric motor.

3. The device of claim 1 wherein the vibratory mechanism comprises an electric linear motor coil and magnet.

4. The device of claim 1 wherein the controller is a multi-layer printed circuit board.

5. The device of claim 1 wherein the controller is suitably adapted to substantially simultaneously activate the vibratory mechanism and the timer and to substantially simultaneously deactivate the vibratory mechanism and the timer.

6. The device of claim 1 wherein the display means of the timer is a liquid crystal display (LCD) screen positioned within an aperture formed in the housing.

7. The device of claim 1 wherein the display means of the timer is a light emitting diode (L.E.D.) display screen positioned within an aperture formed in the housing.

8. The device of claim 1 wherein the power supply comprises one or more disposable batteries.

9. The device of claim 1 wherein the power supply comprises one or more rechargeable batteries.

10. The device of claim 1 wherein the power supply comprises a first power supply and a second power supply,
with said first power supply being suitably adapted to provide power to the vibratory mechanism and said second power supply being suitably adapted to provide power to the timer.

11. A digital tuning fork device for administering a vibratory sensation test to a human subject, comprising
a housing,
said housing being substantially hollow, having an interior and an exterior, constructed of a substantially rigid, durable material, and having a shape suitable for being grasped by a human hand;
a vibratory mechanism,
said vibratory mechanism being contained within the interior of the housing, said vibratory mechanism being electronically powered and suitably adapted to create variable amplitude vibrations at a constant frequency, and further suitably adapted to provide vibrations with amplitudes which decrease in a defined manner over a period of time;
a contact member,
said contact member being substantially elongate and rigid and having an internal end located within the interior of the housing and an external end located exterior of the housing, said internal end suitably adapted to receive vibrations created by the vibratory mechanism and said external end suitably adapted to transmit vibrations to the human subject;
a timer,
said timer being contained within the interior of the housing, said timer being suitably adapted to record the relative passage of time in known units beginning when activated and terminating when deactivated, said timer having a display means for displaying the units of time during activation and the final unit achieved upon deactivation, said display means being capable of being perceived from the exterior of the housing;
a controller,
said controller being contained within the interior of the housing and being suitably adapted to receive input from the exterior of the housing, said controller being suitably adapted to activating and deactivating the vibratory mechanism, activating and deactivating the timer, and resetting the timer;
a power supply,
said power supply being contained within the interior of the housing and being suitably adapted to provide power to the vibratory mechanism and to the timer; and
user input controls,
said user input controls being in connection with the controller and being suitably adapted to allow a user to signal when the power supply is to be activated and deactivated, when the vibratory mechanism is to be activated and deactivated, when the timer is to be activated and deactivated, and when the display means is to be reset;
wherein the user input controls comprise
a power button, with said power button being accessible from the exterior of the housing, said power button being suitably adapted to activate and deactivate the power supply;
an enable button, with said enable button being accessible from the exterior of the housing, said enable button being suitably adapted to activate and deactivate the timer and to activate and deactivate the vibratory mechanism; and
a reset button, with said reset button being accessible from the exterior of the housing, said reset button being suitably adapted to reset the display means.

12. The device of claim 11 wherein the user input controls further comprise
a frequency selection button in connection with the controller and being suitably adapted to allow a user to signal the controller to change the frequency of the vibrations generated by the vibratory mechanism.

13. The device of claim 11 wherein the user input controls further comprise
an amplitude selection button in connection with the controller and being suitably adapted to allow a user to signal the controller to change the beginning amplitude of the vibrations generated by the vibratory mechanism.

14. The device of claim 11 wherein the user input controls further comprise
a degradation selection button in connection with the controller and being suitably adapted to allow a user to signal the controller to change the manner in which the amplitude of the vibrations generated by the vibratory mechanism decrease over time.

15. A method for using a digital tuning fork device for administering a vibratory sensation test to a human subject, said digital tuning fork device comprising
a housing,
said housing being substantially hollow, having an interior and an exterior, constructed of a substantially rigid, durable material, and having a shape suitable for being grasped by a human hand;

a vibratory mechanism,
  said vibratory mechanism being contained within the interior of the housing, said vibratory mechanism being electronically powered and suitably adapted to create variable amplitude vibrations at a constant frequency, and further suitably adapted to provide vibrations with amplitudes which decrease in a defined manner over a period of time;
a contact member,
  said contact member being substantially elongate and rigid and having an internal end located within the interior of the housing and an external end located exterior of the housing, said internal end suitably adapted to receive vibrations created by the vibratory mechanism and said external end suitably adapted to transmit vibrations to the human subject;
a timer,
  said timer being contained within the interior of the housing, said timer being suitably adapted to record the relative passage of time in known units beginning when activated and terminating when deactivated, said timer having a display means for displaying the units of time during activation and the final unit achieved upon deactivation, said display means being capable of being perceived from the exterior of the housing;
a controller,
  said controller being contained within the interior of the housing and being suitably adapted to receive input from the exterior of the housing, said controller being suitably adapted to activating and deactivating the vibratory mechanism, activating and deactivating the timer, and resetting the timer; and
a power supply,
  said power supply being contained within the interior of the housing and being suitably adapted to provide power to the vibratory mechanism and to the timer;
wherein the contact member is movable in relation to the housing, said contact member having a spring to bias the external end of the contact member away from the housing, said contact member being in connection with controller, with movement of the contact member relative to the housing suitably adapted to signal the controller,
such that when the contact member is pressed against a surface the external end of the contact member moves toward the housing causing the contact member to signal the controller to reset the display means, to activate the vibratory mechanism, and to activate timer, and
when the contact member is removed from a surface the biasing spring moves the external end of the contact member away from housing causing the contact member to signal the controller to deactivate the vibratory mechanism and to deactivate timer, said method comprising the following steps:
step A. obtain the digital tuning fork device;
step B. uncover a portion of a patient's body so that the outer skin is revealed;
step C. take the digital tuning fork device in hand;
Step D. place the digital tuning fork device against the uncovered portion of the patient's body;
Step E. activate the vibratory mechanism and timer;
Step F. wait for the patient to indicate a lack of perception of sensation from the vibrations;
Step G. deactivate the vibratory mechanism and stop the timer;
Step H. remove the digital tuning fork device from contact with the patient's body part;

Step I. note the time displayed on the timer display; and
Step J. compare the time displayed on the timer display against known values;
whereby step B is performed in any order relative to steps A and C; step A must be performed before step C; steps A through C must be performed before step D; steps D and E may be performed in any order relative to each other; steps D and E must be performed before step F; steps G and H may be performed in any order relative to each other; step F must be performed before steps G and H; steps I and J must be performed after step G; and step J must be performed after step I.

16. The method of claim 15 further comprising the additional step of:
Step K. make a diagnosis;
whereby step K is performed after step J.

17. The method of claim 15 further wherein step B is eliminated and step D is modified as follows:
Step D. place the digital tuning fork device against a covered portion of the patient's body.

18. A method for using a digital tuning fork device for administering a vibratory sensation test to a human subject, said digital tuning fork device comprising
a housing,
  said housing being substantially hollow, having an interior and an exterior, constructed of a substantially rigid, durable material, and having a shape suitable for being grasped by a human hand;
a vibratory mechanism,
  said vibratory mechanism being contained within the interior of the housing, said vibratory mechanism being electronically powered and suitably adapted to create variable amplitude vibrations at a constant frequency, and further suitably adapted to provide vibrations with amplitudes which decrease in a defined manner over a period of time;
a contact member,
  said contact member being substantially elongate and rigid and having an internal end located within the interior of the housing and an external end located exterior of the housing, said internal end suitably adapted to receive vibrations created by the vibratory mechanism and said external end suitably adapted to transmit vibrations to the human subject;
a timer,
  said timer being contained within the interior of the housing, said timer being suitably adapted to record the relative passage of time in known units beginning when activated and terminating when deactivated, said timer having a display means for displaying the units of time during activation and the final unit achieved upon deactivation, said display means being capable of being perceived from the exterior of the housing;
a controller,
  said controller being contained within the interior of the housing and being suitably adapted to receive input from the exterior of the housing, said controller being suitably adapted to activating and deactivating the vibratory mechanism, activating and deactivating the timer, and resetting the timer;
a power supply,
  said power supply being contained within the interior of the housing and being suitably adapted to provide power to the vibratory mechanism and to the timer; and user input controls,
  said user input controls being in connection with the controller and being suitably adapted to allow a user to signal when the power supply is to be activated and deactivated, when the vibratory mechanism is to be activated and deactivated, when the timer is to be activated and deactivated, and when the display means is to be reset;
wherein the user input controls comprise
  a power button, with said power button being accessible from the exterior of the housing, said power button being suitably adapted to activate and deactivate the power supply;
  an enable button, with said enable button being accessible from the exterior of the housing, said enable button being suitably adapted to activate and deactivate the timer and to activate and deactivate the vibratory mechanism; and
  a reset button, with said reset button being accessible from the exterior of the housing, said reset button being suitably adapted to reset the display means, said method comprising the following steps:
step A. obtain the digital tuning fork device;
step B. uncover a portion of a patient's body so that the outer skin is revealed;
step C. take the digital tuning fork device in hand;
Step D. place the digital tuning fork device against the uncovered portion of the patient's body;
Step E. activate the vibratory mechanism and timer;
Step F. wait for the patient to indicate a lack of perception of sensation from the vibrations;
Step G. deactivate the vibratory mechanism and stop the timer;
Step H. remove the digital tuning fork device from contact with the patient's body part;
Step I. note the time displayed on the timer display; and
Step J. compare the time displayed on the timer display against known values;
whereby step B is performed in any order relative to steps A and C; step A must be performed before step C; steps A through C must be performed before step D; steps D and E may be performed in any order relative to each other; steps D and E must be performed before step F; steps G and H may be performed in any order relative to each other; step F must be performed before steps G and H; steps I and J must be performed after step G; and step J must be performed after step I.

19. The method of claim 18 further comprising the additional step of:
  Step K. make a diagnosis;
  whereby step K is performed after step J.

20. The method of claim 18 further wherein step B is eliminated and step D is modified as follows:
  Step D. place the digital tuning fork device against a covered portion of the patient's body.

* * * * *